United States Patent [19]
Lu et al.

[11] Patent Number: 5,989,930
[45] Date of Patent: Nov. 23, 1999

[54] METHOD FOR OBSERVING TUNGSTEN PLUG OF SEMICONDUCTOR DEVICE MICROSCOPICALLY

[75] Inventors: Shu-Ying Lu, Shinchu; Fei-Chun Tseng, Hsinchu, both of Taiwan

[73] Assignee: United Microelectronics Corp., Taiwan

[21] Appl. No.: 08/805,678

[22] Filed: Feb. 27, 1997

[30] Foreign Application Priority Data

Dec. 26, 1996 [TW] Taiwan ................................. 85116101

[51] Int. Cl.⁶ .................................................. G01R 21/00
[52] U.S. Cl. ................... 438/17; 438/16; 438/18; 438/648; 438/683; 438/685; 438/785
[58] Field of Search ................... 438/658, 632, 438/636, 637, 17, 253, 586, 16, 18, 648, 683, 685, 785

[56] References Cited

U.S. PATENT DOCUMENTS 5,736,863 4/1998 Liu ............................. 324/765

OTHER PUBLICATIONS

Nanda, Characterization of the nucleation and growth process of CVD–W on TiN substrates, Materials Research Society, 401–406, 1995.

Ting, Reduction in flux divergence at vias for improved electromigration in multilayered AlCu interconnects, Applied Physics Letters, 2134–2136, Sep. 30, 1996.

*Primary Examiner*—Charles Bowers
*Assistant Examiner*—Reneé R. Berry
*Attorney, Agent, or Firm*—Rabin & Champagne PC

[57] ABSTRACT

A method of observing a tungsten plug of a semiconductor device using a microscope includes cutting the semiconductor device at the center of the tungsten plug. The semiconductor device is then stained with a reagent which includes hydrogen peroxide and ammonia and etched with a solution containing hydrofluoric acid. The fine structure of the grain of the tungsten plug of the semiconductor device is then observed with a microscope.

13 Claims, 1 Drawing Sheet

METHOD FOR OBSERVING TUNGSTEN PLUG OF SEMICONDUCTOR DEVICE MICROSCOPICALLY

BACKGROUND OF THE INVENTION

1. Field of the Invention

The invention relates in general to a technique for observing a semiconductor device microscopically, and more particularly to a technique that uses reagent to aid in the microscopic observation of a semiconductor device.

2. Description of the Related Art

In a semiconductor device, a tungsten plug is usually used to connect two conducting layers to form a complete circuit. Therefore, the quality of the tungsten plug affects the quality of the semiconductor device. To control the reliability of the semiconductor device manufacturing process, the fine structure of a sample semiconductor device should be observed on a microscopic level. For example, the scale of the tungsten plug and the thickness of a glue layer can be learned by observing the device with a microscope.

A conventional semiconductor device may have a contact window of a tungsten plug that is larger than 0.5 $\mu$m. The tungsten plug can be cut at the center. By etching with a glass reactive solution or a polysilicon reactive solution, for example, a solution of hydrofluoric acid (HF), a solution of hydrofluoric acid and acetic acid ($CH_3COOH$), or a solution of hydrofluoric acid and aqua fortis, the orientation of the grain of the tungsten plug and the structure and thickness of the glue layer 12 can be observed with a microscope.

Because of the rising level of integration, the width of the contact window of the tungsten plug may be less than 0.5 $\mu$m. Therefore, the tungsten plug 20 cannot be cut at the center to show its grain orientation clearly.

To reduce the problem stated above, the center of the tungsten plug 30 is polished after cutting through the tungsten plug. Next, an etching process is performed with an etchant such as those noted above. Finally, the semiconductor device is observed using a scanning electron microscope (SEM). However, the surface of the tungsten is difficult to observe with respect to the grain structure of the tungsten plug and the thickness of the glue layer because the polishing planarizes the surface of the tungsten.

SUMMARY OF THE INVENTION

It is therefore an object of the invention to provide a method for observing the tungsten plug of a semiconductor device microscopically. A method for observing the tungsten plug of a semiconductor device microscopically according to the invention includes cutting the device at the center of the tungsten plug. The semiconductor device is stained with a reagent which includes hydrogen peroxide and ammonia. The tungsten plug is then observed with a microscope. By doing so, the fine grain structure of the tungsten plug and the thickness of the glue layer can be observed, which is useful in controlling the reliability of the semiconductor device manufacturing process.

BRIEF DESCRIPTION OF THE DRAWINGS

Other objects, features, and advantages of the invention will become apparent from the following detailed description of the preferred but non-limiting embodiment. The description is made with reference to the accompanying drawings in which.

DESCRIPTION OF THE PREFERRED EMBODIMENT

Figure 1:
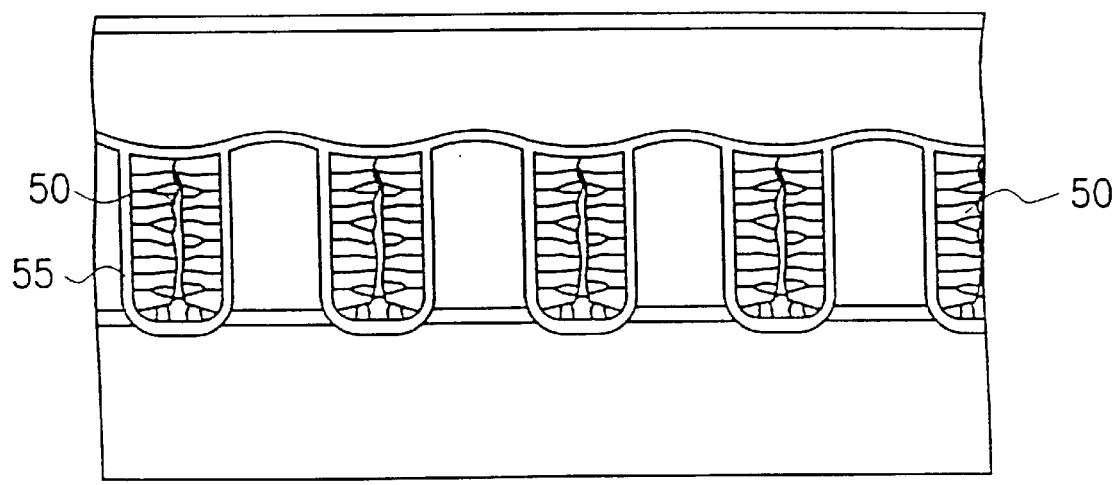
FIG. 1 is a cross-sectional view of the tungsten plug of the semiconductor device according to a preferred embodiment of the invention.

FIG. 1 is respectively a microscopic view and a cross-sectional view obtained according to a preferred embodiment of the invention.

The method according to the invention is used for observing the tungsten plug of a semiconductor device with a microscope. First a semiconductor device with a tungsten plug 50 is provided. Next, the tungsten plug 50 is cut at its center. Then, after polishing, the semiconductor device is stained with a staining reagent which includes hydrogen peroxide and ammonia ($NH_4OH$). For example, the reagent may include $H_2O_2$, $NH_4OH$, and $H_2O$. A suitable ratio of $H_2O_2:NH_4OH:H_2O$ is about 5~25:0.1~10:0.5~20, for example, and a suitable duration of such staining is between about 5 seconds and about 5 minutes, for example. Next, the semiconductor device is etched using a glass reactive solution or a polysilicon reactive solution. For example, a solution of hydrofluoric acid, a solution of hydrofluoric acid and acetic acid, or a solution of hydrofluoric acid and aqua fortis, is used. Finally, the tungsten plug 50 is observed microscopically using, for example, a scanning electron microscope (SEM), a transmitter electron microscope (TEM), or a focused ion beam (FIB).

By polishing the tungsten plug and then staining with reagent which includes hydrogen peroxide and ammonia before etching with a glass solution or a polysilicon solution, the structure and orientation of the tungsten plug 50 and the thickness of the glue layer 55 can be observed clearly. That is, the structure of each layer, such as the grain and the glue layer, can be clearly observed microscopically. Such observation is very helpful to the manufacturing process, for example, in the reliable control, measurement and analysis of the semiconductor device.

While the invention has been described by way of example and in terms of a preferred embodiment, it is to be understood that the invention is not limited thereto. To the contrary, it is intended to cover various modifications and similar arrangements and procedures, and the scope of the appended claims therefore should be accorded the broadest interpretation so as to encompass all such modifications and similar arrangements and procedures.

What is claimed is:

1. A method for microscopic observation of a tungsten plug of a semiconductor device including:

providing a semiconductor device which includes a tungsten plug;

cutting the semiconductor device at the center of the tungsten plug;

staining the cut semiconductor device with a staining reagent comprising hydrogen peroxide and ammonia; and observing the tungsten plug of the stained semiconductor device microscopically.

2. A method according to claim 1, wherein the staining reagent further includes water, and wherein the ratio of hydrogen peroxide:ammonia:water of the staining reagent is about 5~25:0.1~10:0.5~20.

3. A method according to claim 1, wherein the staining with the staining reagent is performed for a duration of about 5 seconds to about 5 minutes.

4. A method according to claim 1, further including etching the semiconductor device with a solution containing hydrofluoric acid after the staining of the semiconductor.

5. A method according to claim 4, wherein the solution includes acetic acid.

6. A method according to claim 4, wherein the solution includes aqua fortis.

7. A method according to claim 1, wherein the observation of the tungsten plug is performed with a scanning electron microscope.

8. A method according to claim 1, wherein the observation of the tungsten plug is performed with a transmitter electron microscope.

9. A method according to claim 1, wherein the observation of the tungsten plug is performed with a focused ion beam.

10. A method according to claim 1, further comprising etching the semiconductor device using one of a glass reactive solution or a polysilicon reactive solution after the staining.

11. A method according to claim 1, further comprising polishing the semiconductor device between the cutting and the staining.

12. A method for microscopic observation of a tungsten plug of a semiconductor device, comprising:

providing a semiconductor device which includes a tungsten plug;

cutting the semiconductor device at the center of the tungsten plug;

staining the cut semiconductor device with a staining reagent comprising hydrogen peroxide and ammonia;

etching the stained semiconductor device; and observing the tungsten plug of the etched semiconductor device microscopically.

13. A method for microscopic observation of a tungsten plug of a semiconductor device, comprising:

providing a semiconductor device which includes a tungsten plug;

cutting the semiconductor device at the center of the tungsten plug;

polishing the cut semiconductor device;

staining the cut semiconductor device with a staining reagent comprising hydrogen peroxide and ammonia;

etching the stained semiconductor device; and observing the tungsten plug of the etched semiconductor device microscopically.

* * * * *